US008619243B2

(12) United States Patent
Ohno et al.

(10) Patent No.: US 8,619,243 B2
(45) Date of Patent: Dec. 31, 2013

(54) MOBILITY MEASURING APPARATUS, METHOD THEREFOR, AND RESISTIVITY MEASURING APPARATUS AND METHOD THEREFOR

(75) Inventors: Seigo Ohno, Wako (JP); Hiromasa Ito, Wako (JP); Hiroaki Minamide, Wako (JP); Akihide Hamano, Tsukuba (JP)

(73) Assignees: Riken, Saitama (JP); Furukawa Co., Ltd., Tokyo (JP)

( * ) Notice: Subject to any disclaimer, the term of this patent is extended or adjusted under 35 U.S.C. 154(b) by 324 days.

(21) Appl. No.: 12/872,385

(22) Filed: Aug. 31, 2010

(65) Prior Publication Data

US 2011/0058155 A1    Mar. 10, 2011

(30) Foreign Application Priority Data

Sep. 4, 2009   (JP) ................................ 2009-204352

(51) Int. Cl.

| G01J 3/00  | (2006.01) |
| H01L 29/04 | (2006.01) |
| H01L 27/14 | (2006.01) |
| H01L 29/12 | (2006.01) |

(52) U.S. Cl.
USPC .......... 356/51; 257/E27.111; 257/59; 257/72; 257/E21.413; 257/43

(58) Field of Classification Search
USPC ..................... 356/51; 257/59, 72, E21.413
See application file for complete search history.

(56) References Cited

U.S. PATENT DOCUMENTS

| 7,649,633 B2 * | 1/2010 | Kawate ........................ 356/504 |
| 2001/0029436 A1 * | 10/2001 | Fukasawa ..................... 702/117 |
| 2010/0091266 A1 * | 4/2010 | Yasuda et al. .................. 356/51 |
| 2010/0271618 A1 * | 10/2010 | Ito et al. ......................... 356/51 |

FOREIGN PATENT DOCUMENTS

JP    2009-145223    2/2009

OTHER PUBLICATIONS

Y. Fu et al. "Electron mobilities, Hall factors, and scattering processes of n-type GaN epilayers studied by infrared reflection and Hall measurements"; Physical Review B vol. 67 (2003), 113313.

(Continued)

*Primary Examiner* — Roy M Punnoose
*Assistant Examiner* — Sunghee Y Gray
(74) *Attorney, Agent, or Firm* — Rankin, Hill & Clark LLP (57) ABSTRACT

A mobility measuring apparatus includes a storage unit that respectively stores a relationship between the mobility $\mu$ of carriers in a semiconductor and a decay constant $\gamma$ of the carriers and a relationship between a reflectivity R of the semiconductor to a terahertz light and the decay constant $\gamma$ of the carriers, a light radiating unit that radiates a terahertz light to the semiconductor as a sample, a detecting unit that detects a reflected light of the sample to the radiated terahertz light, a reflectivity calculating unit that calculates the reflectivity $R_{exp}$ of the sample by determining a ratio of an intensity of the reflected light relative to an intensity of the radiated terahertz light, an obtaining unit that obtains the decay constant $\gamma_{exp}$ of the sample corresponding to the reflectivity $R_{exp}$ of the sample by making reference to the stored relationship between the reflectivity R and the decay constant $\gamma$ of the carriers, and a mobility calculating unit that calculates the mobility $\mu_{exp}$ of the sample from the stored relationship between the mobility $\mu$ and the decay constant $\gamma$ on the basis of the obtained decay constant $\gamma_{exp}$.

15 Claims, 7 Drawing Sheets

(56) References Cited

OTHER PUBLICATIONS

R.T. Holm et al.; "Infrared reflectance studies of bulk and epitaxial-film n-type GaAs"; Journal of Applied Physics, vol. 48, No. 1, (1977), pp. 212-223.

C. Kittel et al.; "Introduction to Solid State Physics 7th edition, former half volume"; Maruzen Co., Ltd., 1998.

C. Wetzel et al.; "Carrier localization of as-grown n-type gallium nitride under large hydrostatic pressure"; Physical Review B vol. 53, No. 3, (1996) pp. 1322-1326.

H. Ito et al.; "Random frequency accessible broad tunable terahertz-wave source using phase-matched 4-dimethylamino-n-methyl-4-stilbazolium tosylate crystal"; Japanese Journal of Applied Physics vol. 46 No. 11, (2007), pp. 7321-7324.

\* cited by examiner

MOBILITY MEASURING APPARATUS, METHOD THEREFOR, AND RESISTIVITY MEASURING APPARATUS AND METHOD THEREFOR

This application is based on Japanese Patent Application No. 2009-204352, the content of which is incorporated hereinto by reference.

BACKGROUND

1. Technical Field

The present invention relates to a mobility measuring apparatus for measuring a mobility of carriers in a semiconductor, a method therefor, and a resistivity measuring apparatus for measuring an electric resistivity of a semiconductor and a method therefor.

2. Related Art

A Hall measurement is generally carried out for measurement of mobility of carriers in a semiconductor and an electric resistivity of a semiconductor.

Also, Fu, et al. (Y. Fu, M. Willander, Z.-F. Li and W. Lu: "Electron mobilities, Hall factors, and scattering processes of n-type GaN epilayers studied by infrared reflection and Hall measurements." Physical Review B Vol. 67(2003) p. 113313) discloses a method of determining the decay constant and the density of the carriers using terahertz waves. By this method, terahertz waves of a broad band including the band of a phonon frequency of a semiconductor are radiated onto a sample so as to observe reflection spectra. Subsequently, fitting is carried out so that the observed reflection spectra and the calculated reflection spectra may be matched with each other, whereby the decay constant and the density of the carriers are determined.

Also, as a method of determining the carrier density of a semiconductor by using two terahertz waves, there is a method disclosed in Japanese Patent Application Laid-open (JP-A) No. 2009-145223.

However, the conventional techniques disclosed in the above documents leave room for improvements with respect to the following points.

The Hall measurement is a contact measurement in which a solder is heated to attach electrodes to a sample; and the four terminals are contacted with the electrodes. In order to attach the electrodes, the sample must be processed into a flat plane, so that this will be a destructive test.

Also, according to the technique disclosed in Fu, et al., terahertz waves of a broad band are radiated onto a sample so as to observe reflection spectra, thereby needing a period of time of several ten minutes. Also, in order to match the observed reflection spectra with the calculated values, calculation must be made for each of the observed reflection spectra. Also, for performing fitting, a period of time of several ten seconds will further be needed.

Further, according to the technique of JP-A No. 2009-145223, the relationship between the reflectivity of a semiconductor to a terahertz light and the decay constant of the carriers is not made clear, so that neither the mobility of the carriers nor the electric resistivity can be determined.

The present invention has been made in view of the aforementioned circumstances, and an object thereof is to provide calculation of a mobility of carriers in a semiconductor and an electric resistivity of a semiconductor in a short period of time in a non-destructive manner.

SUMMARY

In one embodiment, there is provided a mobility measuring apparatus for measuring a mobility $\mu$ of carriers in a semiconductor, including:

a storage unit that respectively stores a relationship between the mobility $\mu$ and a decay constant $\gamma$ of the carriers and a relationship between a reflectivity R of the semiconductor to a terahertz light and the decay constant $\gamma$;

a light radiating unit that radiates a terahertz light to the semiconductor as a sample;

a detecting unit that detects a reflected light of the sample to the radiated terahertz light;

a reflectivity calculating unit that calculates the reflectivity $R_{exp}$ of the sample by determining a ratio of an intensity of the reflected light relative to an intensity of the radiated terahertz light;

an obtaining unit that obtains the decay constant $\gamma_{exp}$ of the sample corresponding to the reflectivity $R_{exp}$ of the sample by making reference to the stored relationship between the reflectivity R and the decay constant $\gamma$; and a mobility calculating unit that calculates the mobility $\mu_{exp}$ of the sample from the stored relationship between the mobility $\mu$ and the decay constant $\gamma$ on the basis of the obtained decay constant $\gamma_{exp}$.

In another embodiment, there is provided a mobility measuring method for measuring a mobility $\mu$ of carriers in a semiconductor, including:

respectively obtaining a relationship between the mobility $\mu$ of the carriers and a decay constant $\gamma$ of the carriers and a relationship between a reflectivity R of the semiconductor to a terahertz light and the decay constant $\gamma$;

radiating a terahertz light to the semiconductor as a sample;

detecting a reflected light of the semiconductor to the radiated terahertz light;

calculating the reflectivity $R_{exp}$ of the sample by determining a ratio of an intensity of the reflected light relative to an intensity of the radiated terahertz light;

obtaining the decay constant $\gamma_{exp}$ of the sample corresponding to the reflectivity $R_{exp}$ of the sample by making reference to the stored relationship between the reflectivity R and the decay constant $\gamma$; and calculating the mobility $\mu_{exp}$ of the sample from the stored relationship between the mobility $\mu$ and the decay constant $\gamma_{exp}$ on the basis of the obtained decay constant $\gamma_{exp}$.

In another embodiment, there is provided an electric resistivity measuring apparatus for measuring an electric resistivity $\rho$ of a semiconductor, including:

a storage unit that respectively stores a relationship between the electric resistivity $\rho$, a decay constant $\gamma$ of carriers in the semiconductor, and a carrier density N, a relationship between a reflectivity R of the semiconductor to a terahertz light and the carrier density N, and a relationship between the carrier density N and the decay constant $\gamma$;

a light radiating unit that radiates a terahertz light to the semiconductor as a sample;

a detecting unit that detects a reflected light of the sample to the radiated terahertz light;

a reflectivity calculating unit that calculates the reflectivity $R_{exp}$ of the sample by determining a ratio of an intensity of the reflected light relative to an intensity of the radiated terahertz light;

an obtaining unit that obtains the carrier density $N_{exp}$ of the sample corresponding to the reflectivity $R_{exp}$ of the sample by making reference to said stored relationship between the reflectivity R and the carrier density N and obtains the decay constant $\gamma_{exp}$ of the sample corresponding to the obtained carrier density $N_{exp}$ by making reference to the stored relationship between the carrier density N and the decay constant $\gamma$; and a resistivity calculating unit that calculates the electric resistivity $\rho_{exp}$ of the sample from the stored relationship between the electric resistivity ρ, the decay constant γ, and the carrier density N on the basis of the obtained carrier density $N_{exp}$ and the obtained decay constant $γ_{exp}$.

In another embodiment, there is provided an electric resistivity measuring method for measuring an electric resistivity ρ of a semiconductor, including:

respectively obtaining a relationship between the electric resistivity ρ, a decay constant γ of carriers in the semiconductor, and a carrier density N, a relationship between a reflectivity R of the semiconductor to a terahertz light and the carrier density N, and a relationship between the carrier density N and the decay constant γ;

radiating a terahertz light to the semiconductor as a sample;

detecting a reflected light of the sample to the radiated terahertz light;

calculating the reflectivity $R_{exp}$ of the sample by determining a ratio of an intensity of the reflected light relative to an intensity of the radiated terahertz light;

obtaining the carrier density $N_{exp}$ of the sample corresponding to the reflectivity $R_{exp}$ of the sample by making reference to the stored relationship between the reflectivity R and the carrier density N and obtaining the decay constant $γ_{exp}$ of the sample corresponding to the obtained carrier density $N_{exp}$ by making reference to the stored relationship between the carrier density N and the decay constant γ; and calculating the electric resistivity $ρ_{exp}$ of the sample from the stored relationship between the electric resistivity ρ, the decay constant γ, and the carrier density N on the basis of the obtained carrier density $N_{exp}$ and the obtained decay constant $γ_{exp}$.

According to the present invention, the relationship between the reflectivity R to the terahertz light of a semiconductor and the decay constant γ of the carriers is obtained in advance. Therefore, by measuring the reflectivity R of a sample to the terahertz light, the corresponding decay constant γ of the carriers can be obtained, whereby the mobility μ of the carriers in the sample can be calculated. Also, by obtaining the relationship between the reflectivity R to the terahertz light of the semiconductor and the carrier density N as well, the corresponding decay constant γ of the carriers and the density N can be obtained by measuring the reflectivity R of the semiconductor to the terahertz light, whereby the electric resistivity ρ of the sample can be calculated. Therefore, the mobility μ of carriers in a semiconductor and the electric resistivity ρ of the semiconductor can be calculated in a short period of time in a non-destructive manner.

According to the present invention, the mobility μ of carriers in a semiconductor and the electric resistivity ρ of the semiconductor can be calculated in a short period of time in a non-destructive manner.

BRIEF DESCRIPTION OF THE DRAWINGS

The above and other objects, advantages, and features of the present invention will be more apparent from the following description of certain preferred embodiments taken in conjunction with the accompanying drawings, in which.

DETAILED DESCRIPTION

The invention will now be described herein with reference to illustrative embodiments. Those skilled in the art will recognize that many alternative embodiments can be accomplished using the teachings of the present invention and that the invention is not limited to the embodiments illustrated for explanatory purposes.

Hereafter, embodiments of the present invention will be described with reference to the attached drawings. Here, in all of the drawings, like constituent elements will be denoted with like reference symbols, and the description thereof will be appropriately omitted.

(First Embodiment)

Figure 1:
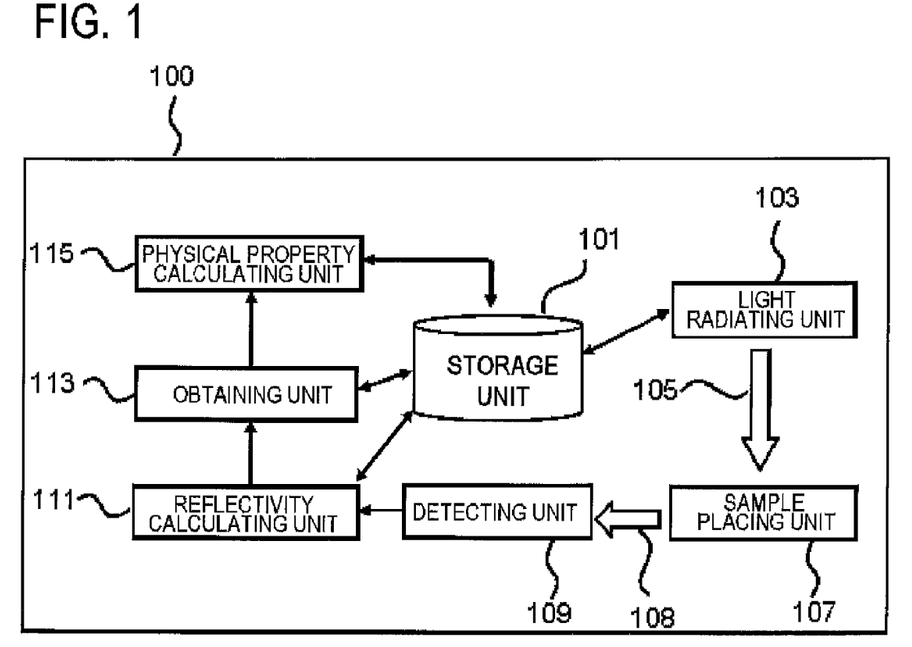
FIG. 1 is a block diagram showing a model of a physical property measuring apparatus according to an embodiment of the present invention.

The present embodiment is a mobility measuring apparatus for measuring a mobility μ of carriers in a semiconductor. FIG. 1 is a block diagram showing a model of a physical property measuring apparatus 100. In the present embodiment, this physical property measuring apparatus 100 is used as a mobility measuring apparatus.

A mobility measuring apparatus according to the present embodiment includes a storage unit 101 that respectively stores a relationship between the mobility μ of carriers in a semiconductor and a decay constant γ of the carriers and a relationship between a reflectivity R of the semiconductor to a terahertz light and the decay constant γ of the carriers, a light radiating unit 103 that radiates a terahertz light 105 to the semiconductor as a sample, a detecting unit 109 that detects a reflected light 108 of the sample to the radiated terahertz light 105, a reflectivity calculating unit 111 that calculates the reflectivity $R_{exp}$ of the sample by determining a ratio of an intensity of the reflected light 108 relative to an intensity of the radiated terahertz light 105, an obtaining unit 113 that obtains the decay constant $γ_{exp}$ of the sample corresponding to the reflectivity $R_{exp}$ of the sample by making reference to the stored relationship between the reflectivity R and the decay constant γ of the carriers, and a physical property calculating unit (mobility calculating unit) 115 that calculates the mobility $μ_{exp}$ of the sample from the stored relationship between the mobility μ and the decay constant γ on the basis of the obtained decay constant $γ_{exp}$.

Also, the physical property measuring apparatus 100 is provided with a sample placing unit 107. The sample placing unit 107 places the semiconductor as a sample.

The semiconductor may be, for example, GaN, SiC, GaAs, GaAlN (aluminum gallium nitride), GaP, GaSb, InN, InP, InAs, InSb, AlN, AlP, AlAs, AlSb, ZnS, ZnSe, ZnTe, CdS, CdSe, CdTe, AlGaP, AlGaAs, AlGaSb, GaInN, GaInP, GaInAs, GaInSb, AlInN, AlInP, AlInAs, AlInSb, Si, Ge, or the like.

The semiconductor may be doped with an impurity. The impurity (additive) used for doping may be of any kind irrespective of whether it is of the p-type or the n-type. For example, as an n-type (donor), silicon, nitrogen, phosphorus, or the like can be used. As the p-type, silicon, boron, or the like can be used.

The storage unit 101 stores, as an equation (1), a relationship between the mobility μ of carriers and the decay constant γ of the carriers. In the equation (1), e represents the electric charge [C] of an electron, and m* represents an effective mass [kg] of the electron.

$$\mu = \frac{e}{m*\gamma} \quad (1)$$

Also, the storage unit 101 stores a relationship between the reflectivity R of the semiconductor to a terahertz light and the decay constant γ of the carriers. The relationship between the reflectivity R and the decay constant γ of the carriers is represented by following equations (2) to (5). The parameters are shown in Table 1. The equation (2) is an equation shown in Holm, et al. (R. T. Holm, J. W. Gibson and E. D. Palik. "Infrared reflectance studies of bulk and epitaxial film n-type GaAs." Journal of Applied Physics, Vol. 48 (1977) p. 212-223).

TABLE 1

| Parameter | | Unit |
|---|---|---|
| ω | frequency | cm$^{-1}$ |
| ε | relative permittivity | |
| $\omega_T$ | TO phonon frequency | cm$^{-1}$ |
| $\omega_L$ | LO phonon frequency | cm$^{-1}$ |
| Γ | decay constant of phonon | |
| $\omega_p$ | plasma frequency | cm$^{-1}$ |
| γ | decay constant of carriers | |
| $\varepsilon_\infty$ | relative permittivity at a sufficiently high frequency | |
| N | carrier density | cm$^{-3}$ |
| e | electric charge | C |
| m* | effective mass of carrier | kg |
| n | refractive index | |
| K | decay coefficient | |
| R | reflectivity | |
| μ | mobility | cm$^2$V$^{-1}$s$^{-1}$ |
| ρ | electric resistivity | Ω cm |
| $R_{rr}$ | relative reflectivity | |

$$\varepsilon(\omega) = \varepsilon_\infty \left(1 - \frac{\omega_T^2 - \omega_L^2}{\omega_T^2 - \omega(\omega - i\Gamma)} - \frac{\omega_p^2}{\omega(\omega - i\gamma)}\right) = (n - i\kappa)^2 \quad (2)$$

The equation (3) is an equation representing the plasma frequency. It is disclosed in Kittel (C. Kittel: Introduction to Solid State Physics 7th edition, former half volume, translated by Ryousei Uno, Noboru Tsuya, Akira Morita, and Jiro Yamashita (Maruzen Co., Ltd., 1998)) that a plasma is a medium made of positive and negative electric charges having an equal density. The frequency at which the plasma is generated is referred to as a plasma frequency. The carrier density N in the equation (3) represents the density of the positive or negative electric charge. The positive one represents the density of free electrons, and the negative one represents the density of holes.

$$\omega_p = \sqrt{\frac{Ne^2}{m*\varepsilon_\infty}} \quad (3)$$

$$R = \frac{(n-1)^2 + \kappa^2}{(n+1)^2 + \kappa^2} \quad (4)$$

Also, the equation (5) is an equation disclosed in Wetzel, et al. (C. Wetzel, W. Walukiewicz, E. E. Haller, J. Ager III, I. Grzegory, S. Porowski and T. Suski. "Carrier Localization of as-grown n-type gallium nitride under large hydrostatic pressure" Physical Review B Vol. 53, (1996) p. 1322-1326). The symbols a, b, and c in the equation (5) are constants.

$$N = a(\omega_L - b)^c \quad (5)$$

Figure 3:
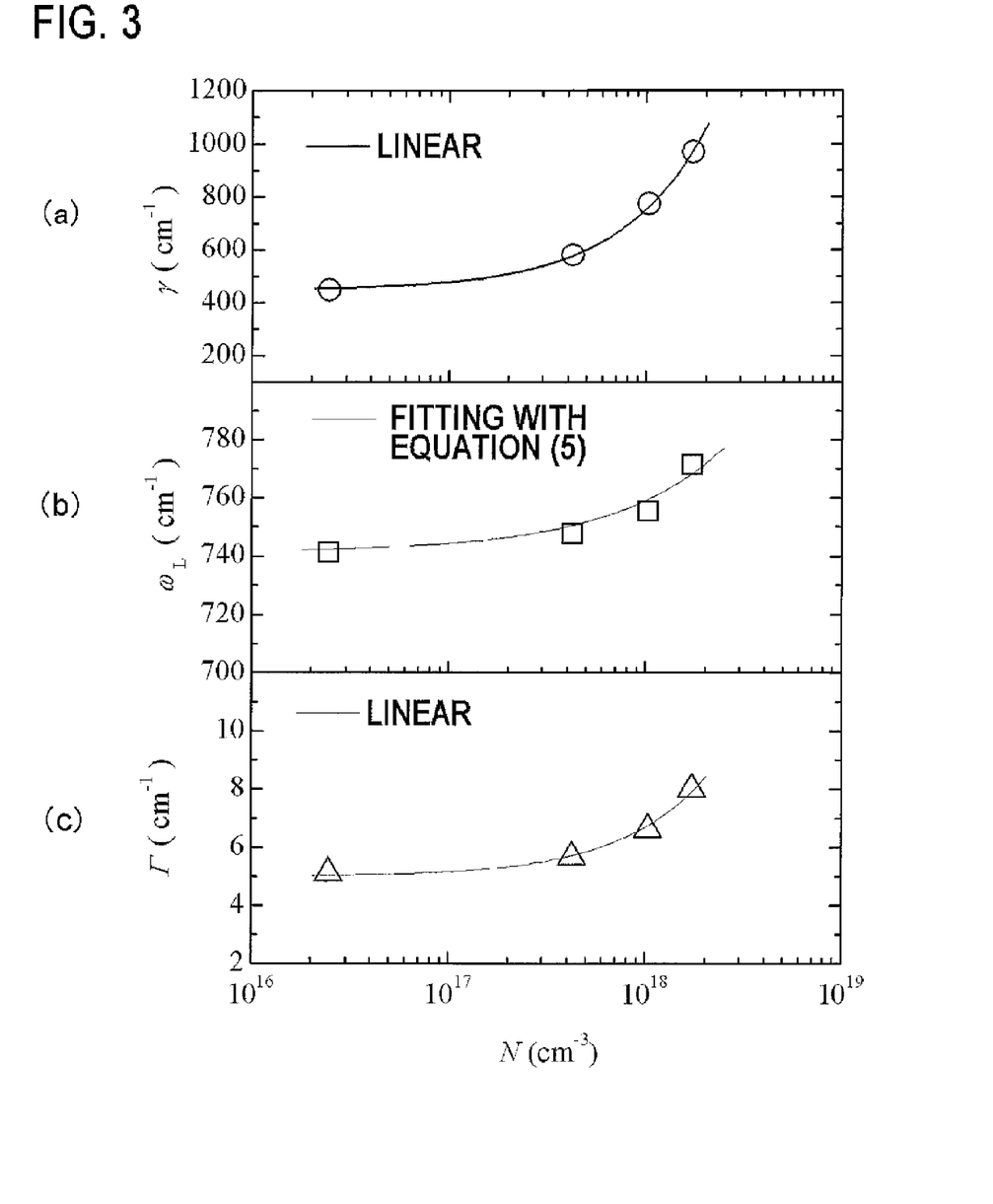
FIG. 3 is a view showing a relationship among the decay constant γ of carriers, the carrier density N, the LO phonon frequency $ω_L$, and the decay constant Γ of phonons.

Also, the decay constant Γ of phonons and the decay constant γ of carriers are represented by a linear relational equation (γ=d×N+e, Γ=f×N+g, d to g are constants) with the carrier density N, as shown in FIGS. 3A and 3C. Therefore, from the reflection spectrum, the relationship between the reflectivity R and the decay constant γ of carriers can be deduced.

Figure 2:
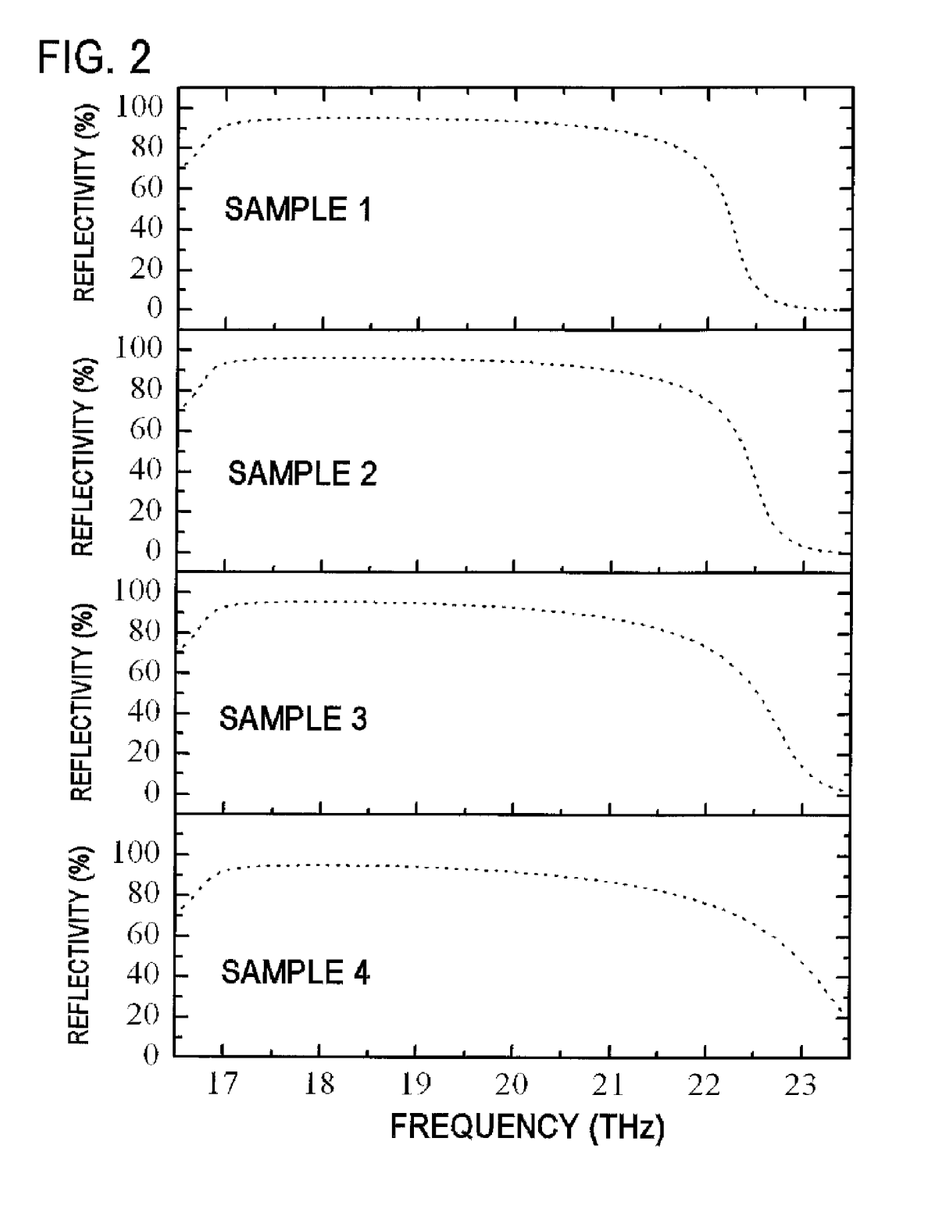
FIG. 2 is a view showing one example of a calculated value of a reflection spectrum.

Also, the reflection spectrum of a semiconductor is always a high reflection in a specific frequency band; however, there is a band in which the shape of this reflection spectrum differs depending on the difference in the LO phonon frequency $\omega_L$, the decay constant Γ of phonons, the decay constant γ of carriers, and the carrier density N. For example, FIG. 2 shows a calculated value of the reflection spectrum when GaN is used as the semiconductor. Table 2 shows the parameters used in the calculations of FIGS. 2 and 3. With respect to GaN, the shape of the reflection spectrum around 22 THz differs depending on the difference in the LO phonon frequency $\omega_L$, the decay constant Γ of phonons, the decay constant γ of carriers, and the carrier density N. On the other hand, the reflection spectrum around 19 THz is always a high reflection.

TABLE 2

| Samples | $\varepsilon_\infty$ | $\omega_T$ (cm$^{-1}$) | $\omega_L$ (cm$^{-1}$) | Γ (cm$^{-1}$) | γ (cm$^{-1}$) | N (10$^{18}$ cm$^{-3}$) | μ (cm$^2$V$^{-1}$s$^{-1}$) | ρ (Ω cm) |
|---|---|---|---|---|---|---|---|---|
| 1 | 5.35 | 560 | 741 | 5.11 | 447 | 0.0246 | 640 | 0.290 |
| 2 | 5.35 | 560 | 747 | 5.67 | 580 | 0.425 | 508 | 0.0291 |
| 3 | 5.35 | 560 | 755 | 6.61 | 774 | 1.03 | 432 | 0.0193 |
| 4 | 5.35 | 560 | 771 | 8.00 | 969 | 1.73 | 302 | 0.0121 |

Therefore, assuming that the band in which the reflectivity R of the semiconductor to the terahertz light changes by depending on the decay constant γ of the carriers is a measurement band and assuming that the band in which the reflectivity R of the semiconductor to the terahertz light does not change by depending on the decay constant γ of the carriers is a reference band, the relative reflectivity $R_{rr}$ can be calculated from an equation (6) assuming that the reflectivity to the terahertz light of the measurement band is a measurement reflectivity $R(\omega_{out})$ and assuming that the reflectivity to the terahertz light of the reference band is a reference reflectivity $R(\omega_{in})$. The storage unit 101 may store the relationship between the calculated relative reflectivity $R_{rr}$ and the decay constant γ of the carriers into the storage unit 101.

$$R_{rr} = \frac{R(\omega_{out})}{R(\omega_{in})} \quad (6)$$

Figure 5:
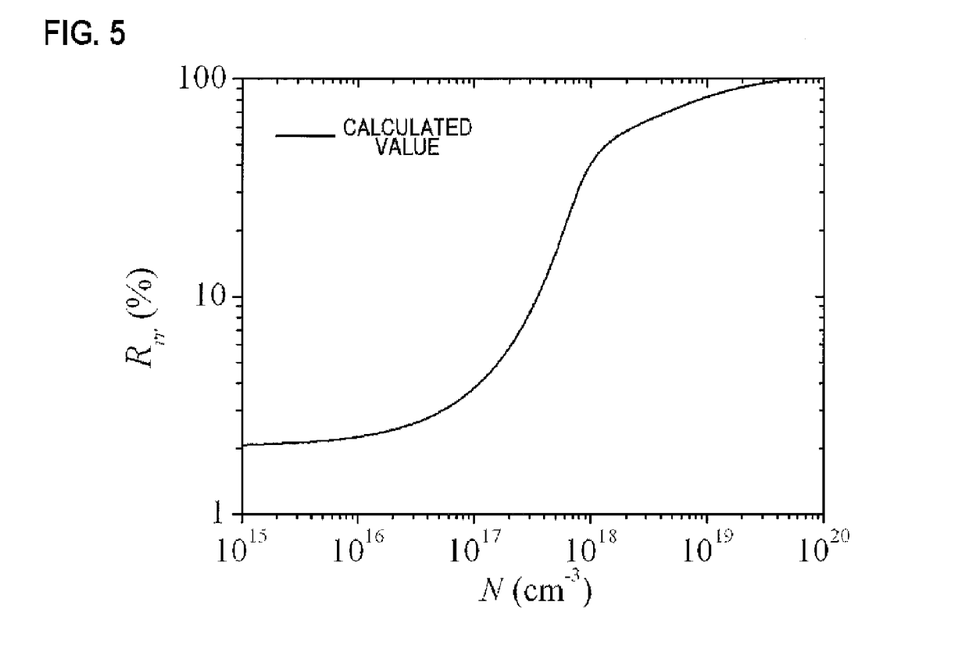
FIG. 5 is a view showing a relationship between the carrier density N and the relative reflectivity $R_{rr}$.

Also, the storage unit 101 can store the relationship between the reflectivity R and the decay constant γ of the carriers by respectively storing the relationship between the decay constant γ of the carriers and the carrier density N shown in FIG. 3A and the relationship between the relative reflectivity $R_{rr}$ of the semiconductor to the terahertz light and the carrier density N shown in FIG. 5.

The light radiating unit 103 allows a second harmonic wave (wavelength: 532 nm) of a Nd:YAG laser (neodymium.YAG laser) to be incident into an optical parametric oscillator that uses a KTP crystal ($KTiOPO_4$), oscillates two wavelengths of 1.3 μm band, allows the two wavelengths to be incident into a DAST crystal (4-dimethylamino-N-methyl-4-stilabazolium-tosylate), so as to radiate an optical wave of a terahertz band of equal to or more than 1.5 THz and equal to or less than 40 THz. Here, another crystal may be used instead of a DAST crystal if a terahertz light can be radiated to the semiconductor constituting a sample. Also, an optical wave of a terahertz band oscillated by using a femtosecond laser can be used as well. The light radiating unit 103 stores information such as the wavelength of the radiated light, the light quantity, and the angle of incidence to the sample into the storage unit 101.

The detecting unit 109 sends the information on the detected reflected light to the reflectivity calculating unit 111. As the detecting unit 109, a DTGS (Deuterated Triglycine Sulfate) detector can be used.

The reflectivity calculating unit 111 receives, from the detecting unit 109, the information on the angle of incidence, the light quantity, and the like of the reflected light detected by the detecting unit 109, and calculates the reflectivity $R_{exp}$ of the sample from the information of the radiated light stored in the storage unit 101 and the received information on the reflected light. The calculated reflectivity $R_{exp}$ is sent out to the obtaining unit 113. Also, the calculated reflectivity $R_{exp}$ may be stored into the storage unit 101 or may be output.

The reflectivity $R_{exp}$ can be measured in the following manner. First, a reference plate (for example, a gold mirror) is placed in the sample placing unit 107. The light obtained by reflection of the radiated light by the gold mirror is defined as a radiated light intensity. Next, a semiconductor is placed in the sample placing unit 107. The light obtained by reflection of the radiated light by the semiconductor is defined as a reflected light intensity. The value obtained by dividing the reflected light intensity by the radiated light intensity is the reflectivity $R_{exp}$.

The obtaining unit 113 makes reference to the storage unit 101 and obtains the corresponding decay constant γ of the carriers from the reflectivity $R_{exp}$ received from the reflectivity calculating unit 111 on the basis of the stored relationship between the reflectivity $R_{exp}$ and the decay constant γ of the carriers. The obtaining unit 113 sends the obtained decay constant γ out to the physical property calculating unit 115.

The physical property calculating unit 115 makes reference to the storage unit 101 and calculates the mobility $\mu_{exp}$ of the carriers in the sample from the stored relationship between the mobility μ of the carriers and the decay constant γ of the carriers. The physical property calculating unit 115 may output the calculated mobility $\mu_{exp}$ of the carriers.

Also, the light radiating unit 103 may respectively radiate the terahertz light of the measurement band and the terahertz light of the reference band to the sample. The reflectivity calculating unit 111 calculates the relative reflectivity $R_{rrexp}$ of the sample by comparing the measurement reflectivity $R(\omega_{out})_{exp}$ calculated when a terahertz light of the measurement band is radiated and the reference reflectivity $R(\omega_{in})_{exp}$ calculated when a terahertz light of the reference band is radiated. The obtaining unit 113 makes reference to the relationship between the relative reflectivity $R_{rr}$ and the decay constant γ of the carriers stored in the storage unit 101, and obtains the decay constant $\gamma_{exp}$ of the carriers corresponding to the calculated relative reflectivity $R_{rrexp}$ of the sample. By substituting the equation (1) with the decay constant $\gamma_{exp}$ of the carriers obtained in this manner, the mobility $\mu_{exp}$ of the carriers in the sample is calculated.

The reference band can be assumed to be a high-reflectivity band between the TO phonon frequency and the LO phonon frequency. The TO phonon frequency and the LO phonon frequency are frequencies at which the relative permittivity becomes 0, and the value of the relative permittivity becomes negative between the TO phonon frequency and the LO phonon frequency. In the range in which the value of the relative permittivity is smaller than 0, a terahertz light is hardly propagated through the semiconductor, so that this will be a high reflection range. The term "high-reflectivity band" as referred to herein refers to a band in which the reflectivity is higher than the reflectivity Rs shown by an equation (7) in the band between the TO phonon frequency and the LO phonon frequency. The symbol n is a square root of the relative permittivity $\epsilon_\infty$ at a sufficiently high frequency. Also, the symbol $n_a$ is a refractive index of ambient air or a refractive index of a medium surrounding the semiconductor.

$$Rs = (n-n_a)^2/(n+n_a)^2 \quad (7)$$

Assuming that $n_a$ is a refractive index of ambient air, $n_a$ is represented as 1. In the case of GaN placed in ambient air, $\sqrt{\epsilon_\infty} = n = 2.31$ holds, and $Rs = (2.31-1)^2/(2.31+1)^2 = 0.156$ holds. Therefore, the reference band of GaN placed in ambient air can be assumed to be a band having a reflectivity higher than about 16% in the band between the TO phonon frequency and the LO phonon frequency.

Hereafter, with reference to the attached drawings, the construction of a physical property measuring apparatus pertaining to the present embodiment will be more specifically described.

Figure 4:
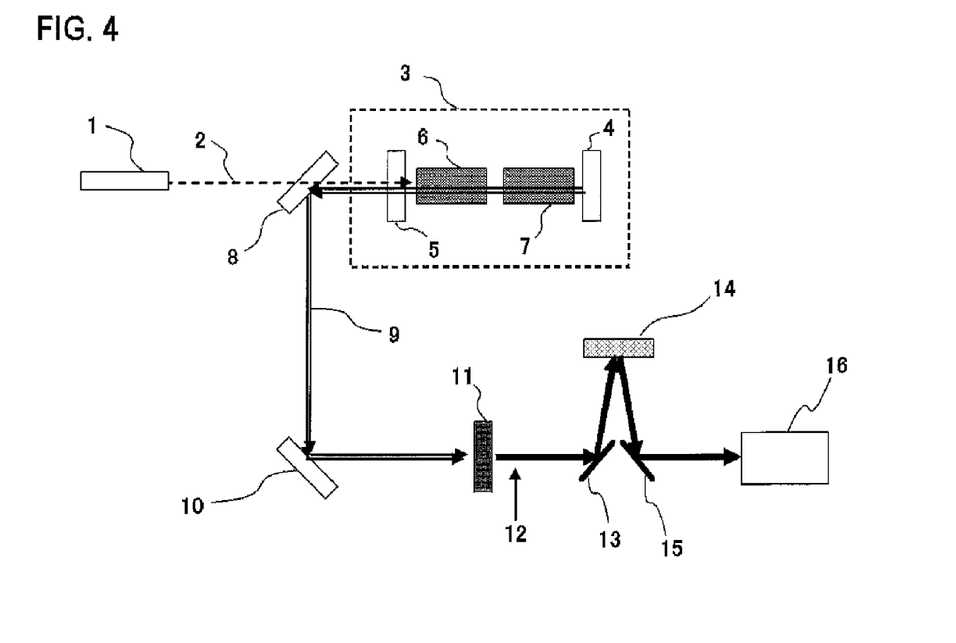
FIG. 4 is a construction view of a physical property measuring apparatus according to an embodiment of the present invention.

FIG. 4 shows one example of a construction view of a physical property measuring apparatus. As a terahertz optical oscillation apparatus, an optical parametric oscillator 3 using a DAST crystal 11 disclosed in Ito, et al. (H. Ito, K. Suizu, T. Yamashita, A. Nawahara and T. Sato, "Random Frequency Accessible Broad Tunable Terahertz-Wave Source Using Phase-Matched 4-dimethylamino-N-methyl-4-stilbazolium Tosylate Crystal," Japanese Journal of Applied Physics Vol. 46 (2007) p. 7321-7324), is used. As the excitation light 2 of the optical parametric oscillator 3, a second harmonic wave (wavelength: 532 nm) of a Nd:YAG laser 1 is used. The excitation light 2 is allowed to be incident into the optical parametric oscillator 3. In the optical parametric oscillator 3, two KTP crystals (KTiOPO$_4$ crystals) having slightly different crystal angles are placed within one resonator constituted of a reflection mirror 4 and a transmission mirror 5, whereby two different wavelengths 9 of a 1.3 μm band are oscillated from the KTP crystals 6, 7. The two wavelengths 9 of the 1.3 μm band are reflected by a reflection mirror 8 and a reflection mirror 10, and is allowed to be incident into the DAST crystal 11, whereby a terahertz light 12 (terahertz wave in FIG. 4) of equal to or more than 1.5 THz and equal to or less than 47 THz can be taken out by the non-linear optical effect. The oscillated terahertz light 12 is reflected by a mirror 13 to be radiated onto a semiconductor 14. The terahertz light 12 reflected by the semiconductor 14 is reflected by a mirror 15, and is received by a DTGS detector 16.

Next, a method of measuring the mobility of carriers will be described using FIG. 1 or 4 by raising GaN as an example. First, the equation (1) is obtained which is a relationship equation between the mobility μ of the carriers and the decay constant γ of the carriers. Subsequently, a relationship between the reflectivity R to the terahertz light of GaN and the decay constant γ of the carriers is obtained. The relationships may be obtained by calculation using the equations (2) to (5), or may be obtained by measuring the reflection spectrum of a sample of GaN as a standard. As a method by calculation, for example, there is a method such that a relationship of the reflectivity R to the frequency of GaN deduced from the samples shown in Table 2 by calculation is examined, whereby a reflection spectrum such as shown in FIG. 2 is obtained. The lateral axis of the spectrum shown in FIG. 2 represents the frequency [THz], and the longitudinal axis represents the reflectivity R. Also, in the spectrum of FIG. 2, there is shown a calculation result on GaN with the decay constants γ of the carriers being 447, 580, 774, and 969 [cm$^{-1}$]. Regarding GaN, the total reflection occurs in the band of equal to or more than 17 THz and equal to or less than 20 THz irrespective of the change in the decay constant γ of the carriers. Also, the reflectivity R changes by the change in the decay constant γ of the carriers in the band of equal to or more than 21 THz and equal to or less than 23 THz. Therefore, assuming that the band of equal to more than 17 THz and equal to or less than 20 THz is a reference band and that the band of equal to or more than 21 THz and equal to or less than 23 THz is a measurement band, the relative reflectivity $R_{rr}$ is determined from the reflectivity $R(\omega_{out})$ in the measurement band relative to the reflectivity $R(\omega_{in})$ in the reference band. Then, as shown in FIG. 5, a relationship between the relative reflectivity $R_{rr}$ and the carrier density N is determined. Also, as shown in FIG. 321, a relationship between the decay constant γ of the carriers in GaN and the carrier density N is determined. By doing so, a relationship between the reflectivity R and the decay constant γ of the carriers can be obtained by assuming the relative reflectivity $R_{rr}$ to be the reflectivity R.

Next, a sample of GaN with an unknown mobility μ of the carriers is prepared and placed in the sample placing unit 107. The light radiating unit 103 radiates a sum of two optical waves respectively to the sample, where one optical wave is a terahertz light of equal to or more than 17 THz and equal to or less than 20 THz in the high-reflection band as a reference band and the other optical wave is a terahertz light of equal to or more than 21 THz and equal to or less than 23 THz at which the reflectivity R changes depending on the decay constant γ of the carriers as a measurement band.

Next, the reference reflectivity $R(\omega_{in})_{exp}$ is calculated by comparing the radiated terahertz light of the reference band and the detected reflected light. Also, the measurement reflectivity $R(\omega_{out})_{exp}$ is calculated by comparing the radiated terahertz light of the measurement band and the detected reflected light. Thereafter, the relative reflectivity $R_{rr}$ of the sample is calculated by comparing the measurement reflectivity $R(\omega_{out})_{exp}$ and the reference reflectivity $R(\omega_{in})_{exp}$ on the basis of the equation (6).

Next, the decay constant $\gamma_{exp}$ of the carriers of the sample corresponding to the calculated relative reflectivity $R_{rrexp}$ of the sample is obtained by making reference to the relationship between the relative reflectivity $R_{rr}$ and the decay constant γ of the carriers that has been obtained in advance.

Then, the mobility $\mu_{exp}$ of the carriers of the sample is calculated by substituting the equation (1) with the obtained decay constant $\gamma_{exp}$ of the carriers.

Next, the functions and effects of the present embodiment will be described. In the present embodiment, a relationship between the reflectivity R of a semiconductor to a terahertz light and the decay constant γ of carriers is obtained in advance. Therefore, by measuring the reflectivity R of a semiconductor to a terahertz light, the corresponding decay constant γ of the carriers can be obtained, whereby the mobility μ of the carriers in the sample can be calculated. Thus, the mobility μ of the carriers in a semiconductor can be measured in a short period of time in a non-destructive manner.

(Second Embodiment)

In the present embodiment, a physical property measuring apparatus 100 shown in FIG. 1 is used as a resistivity measuring apparatus. In the present embodiment, a storage unit 101 respectively stores a relationship between the electric resistivity ρ, the decay constant γ of carriers in a semiconductor, and the carrier density N, a relationship between a reflectivity R of the semiconductor to a terahertz light and the carrier density N, and a relationship between the carrier density N and the decay constant γ. An obtaining unit 113 obtains the carrier density $N_{exp}$ of the sample corresponding to the reflectivity $R_{exp}$ of the sample by making reference to the stored relationship between the reflectivity R and the carrier density N and obtains the decay constant $\gamma_{exp}$ of the carriers of the sample corresponding to the obtained carrier density $N_{exp}$ by making reference to the stored relationship between the carrier density N and the decay constant γ of the carriers. A physical property calculating unit 115 (resistivity calculating unit) calculates the electric resistivity $\rho_{exp}$ of the sample from the stored relationship between the electric resistivity ρ, the decay constant γ, and the carrier density N on the basis of the obtained carrier density $N_{exp}$ and the obtained decay constant $\gamma_{exp}$ of the carriers. The other constructions are the same as in the first embodiment.

The storage unit 101 stores the relationship between the electric resistivity ρ, the decay constant γ of the carriers, and the carrier density κ as an equation (8).

$$\rho = \frac{m*\gamma}{Ne^2} \quad (8)$$

The relationship between the reflectivity R of a semiconductor to a terahertz light and the carrier density N is stored in the storage unit 101 as a graph such as shown in FIG. 5, for example. In FIG. 5, the reflectivity R is shown as a relative reflectivity $R_{rr}$. The relative reflectivity $R_{rr}$ can be determined from the equation (6) as described in the first embodiment.

The relationship between the carrier density N and the decay constant γ of the carriers is stored in the storage unit 101 as a relationship by which the decay constant γ of the carriers changes linearly relative to the carrier density N, as shown in FIG. 3A.

The obtaining unit 113 makes reference to the storage unit 101 and obtains the corresponding carrier density $N_{exp}$ from the reflectivity $R_{exp}$ received from the reflectivity calculating unit 111 on the basis of the stored relationship between the reflectivity R and the carrier density N. The obtaining unit 113 sends the obtained carrier density $N_{exp}$ out to the physical property calculating unit 115.

The physical property calculating unit 115 makes reference to the storage unit 101 and obtains the decay constant $γ_{exp}$ of the carriers in the sample from the stored relationship between the carrier density N and the decay constant γ of the carriers. Further, the physical property calculating unit 115 makes reference to the storage unit 101 and calculates the electric resistivity $ρ_{exp}$ of the sample from the stored relationship between the electric resistivity ρ, the decay constant γ of the carriers, and the carrier density N. The physical property calculating unit 115 may output the calculated electric resistivity ρ.

Also, the light radiating unit 103 may respectively radiate the terahertz light of the measurement band and the terahertz light of the reference band to the sample. The reflectivity calculating unit 111 calculates the relative reflectivity $R_{rrexp}$ of the sample by comparing the measurement reflectivity $R(ω_{out})_{exp}$ calculated when a terahertz light of the measurement band is radiated and the reference reflectivity $R(ω_{in})_{exp}$ calculated when a terahertz light of the reference band is radiated. The obtaining unit 113 makes reference to the relationship between the relative reflectivity $R_{rr}$ and the carrier density N stored in the storage unit 101, and obtains the carrier density $N_{exp}$ corresponding to the calculated relative reflectivity $R_{rrexp}$ of the sample. The decay constant $γ_{exp}$ of the carriers in the sample is obtained from the carrier density $N_{exp}$ obtained in this manner, and the electric resistivity $ρ_{exp}$ of the sample is calculated from the stored relationship between the electric resistivity ρ, the decay constant γ of the carriers, and the carrier density N.

The reference band can be assumed to be a high-reflectivity band between the TO phonon frequency and the LO phonon frequency.

Next, a method of measuring the resistivity will be described using FIG. 1 or 4 by raising GaN as an example. First, the equation (8) is obtained which is a relationship equation between the electric resistivity ρ, the decay constant γ of the carriers, and the carrier density N. Subsequently, a relationship between the reflectivity R to the terahertz light of GaN and the carrier density N is obtained. The relationships may be obtained by calculation using the equations (2) to (5), or may be obtained by measuring the reflection spectrum of a sample of GaN as a standard. As a method by calculation, for example, there is a method such that a relationship of the reflectivity R to the frequency of GaN deduced from the samples shown in Table 2 by calculation is examined, whereby a reflection spectrum such as shown in FIG. 2 is obtained. In the spectrum of FIG. 2, there is shown a calculation result on GaN with the carrier density N being 0.0246, 0.425, 1.03, and 1.73 [×10$^{18}$ cm$^{-3}$]. Assuming that the band of equal to or more than 17 THz and equal to or less than 20 THz is a reference band and that the band of equal to or more than 21 THz and equal to or less than 23 THz is a measurement band, the relative reflectivity $R_{rr}$ is determined from the reflectivity $R(ω_{out})$ in the measurement band relative to the reflectivity $R(ω_{in})$ in the reference band. Then, assuming this relative reflectivity $R_{rr}$ to be the reflectivity R, a relationship such as shown in FIG. 5 between the relative reflectivity $R_{rr}$ and the carrier density N is determined. Also, as shown in FIG. 3A, a relationship between the decay constant γ of the carriers in GaN and the carrier density N is determined.

Next, a sample of GaN with an unknown electric resistivity ρ is prepared and placed in the sample placing unit 107. The light radiating unit 103 radiates a sum of two optical waves respectively to the sample, where one optical wave is a terahertz light of equal to or more than 17 THz and equal to or less than 20 THz in the high-reflection band as a reference band and the other optical wave is a terahertz light of equal to or more than 21 THz and equal to or less than 23 THz at which the reflectivity R changes depending on the carrier density N as a measurement band. Then, the relative reflectivity $R_{rrexp}$ of the sample is obtained by comparing the measurement reflectivity $R(ω_{out})_{exp}$ and the reference reflectivity $R(ω_{in})_{exp}$, as described in the first embodiment.

Next, the carrier density $N_{exp}$ of the sample corresponding to the calculated relative reflectivity $R_{rrexp}$ of the sample is obtained by making reference to the relationship between the relative reflectivity $R_{rr}$ and the carrier density N that has been obtained in advance. Also, the decay constant $γ_{exp}$ of the carriers of the sample corresponding to the calculated relative reflectivity $R_{rrexp}$ of the sample is obtained by making reference to the relationship between the carrier density N and the decay constant γ of the carriers that has been obtained in advance.

Then, the electric resistivity $ρ_{exp}$ of the sample is calculated by substituting the equation (8) with the obtained decay constant $γ_{exp}$ of the carriers and the obtained carrier density $N_{exp}$.

Next, the functions and effects of the present embodiment will be described. In the present embodiment, according to the present invention, a relationship between the reflectivity R of a semiconductor to a terahertz light and the carrier density N and a relationship between the carrier density N and the decay constant γ of the carriers are obtained in advance. Therefore, by measuring the reflectivity R of a semiconductor to a terahertz light, the corresponding decay constant $γ_{exp}$ of the carriers can be obtained, whereby the electric resistivity $ρ_{exp}$ of the sample can be calculated. Thus, the electric resistivity ρ of a semiconductor can be measured in a short period of time in a non-destructive manner.

As shown above, the embodiments of the present invention have been described with reference to the attached drawings; however, these are exemplifications of the present invention, so that various constructions other than the above can be adopted as well.

EXAMPLES

Example 1

Figure 6:
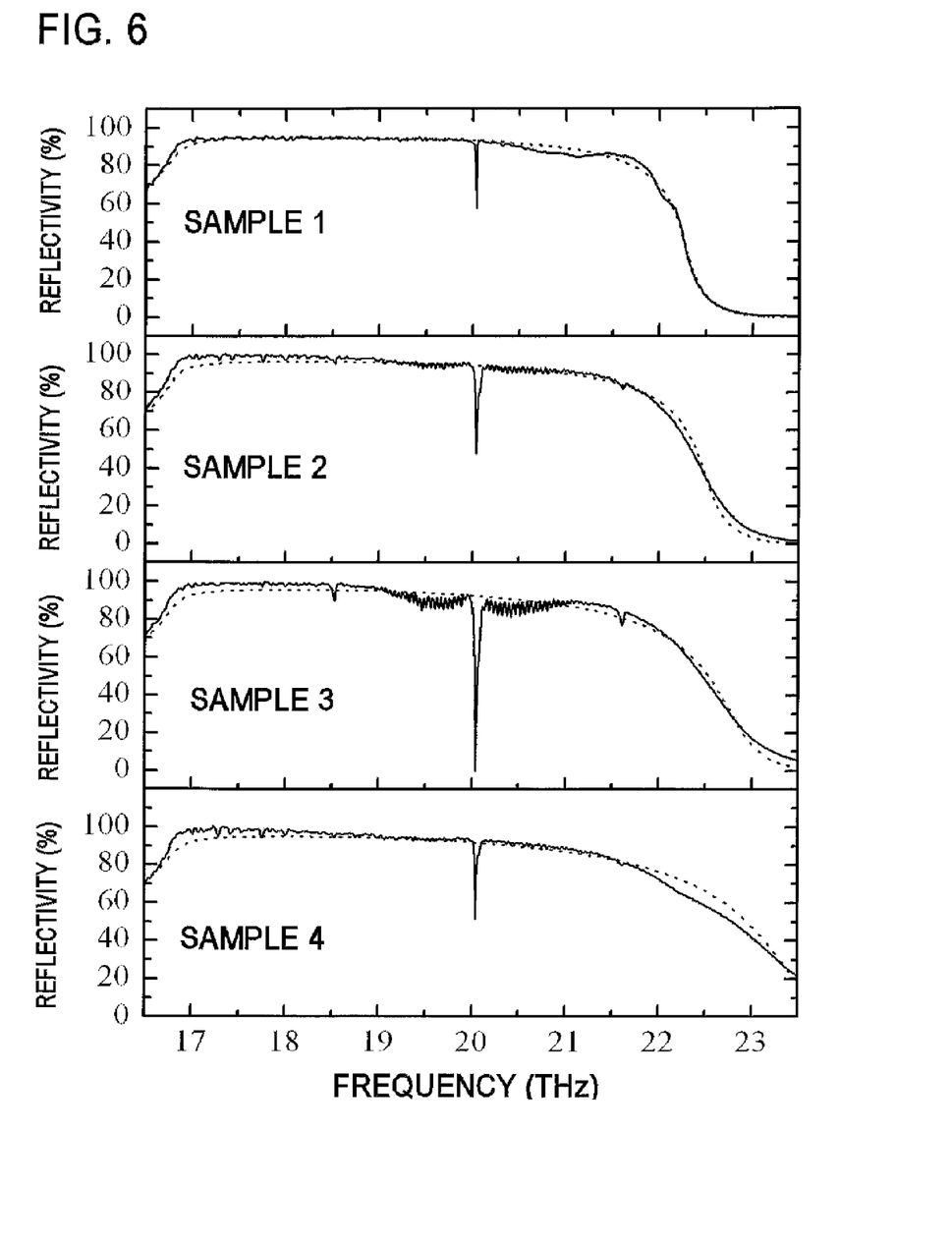
FIG. 6 is a view showing a measured value and a calculated value of the reflection spectrum of GaN.
Figure 7:
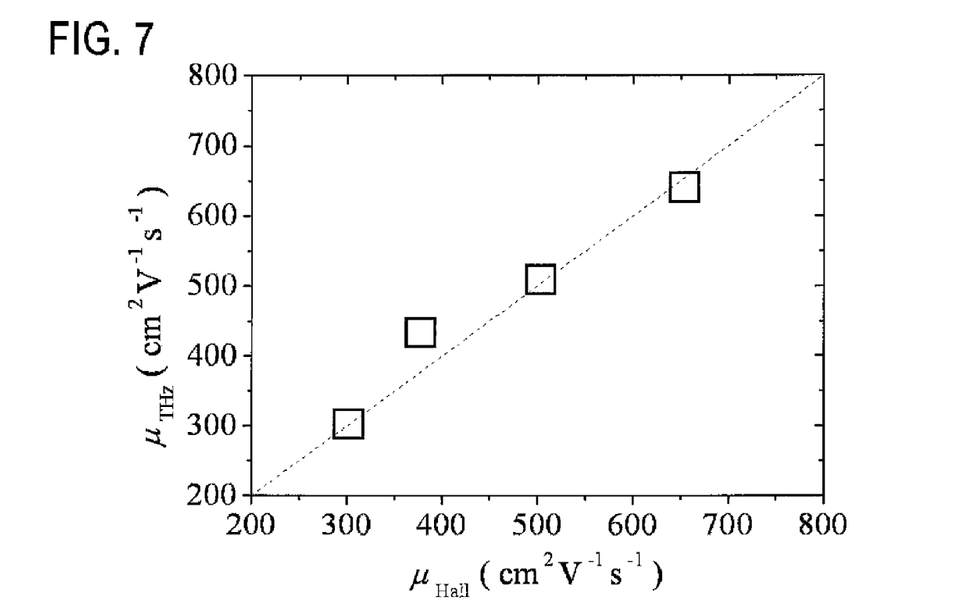
FIG. 7 is a view comparing the Hall measurement result of the mobility μ of the carriers in GaN and the measurement result according to the present invention, where the lateral axis represents the Hall measurement result, and the longitudinal axis represents the measurement result according to the present invention.
Figure 8:
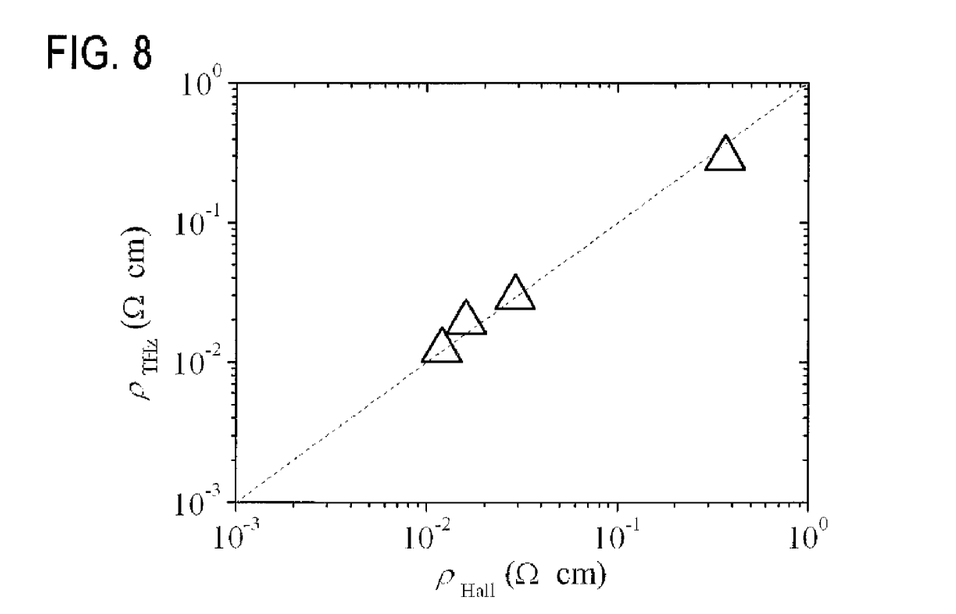
FIG. 8 is a view comparing the Hall measurement result of the electric resistivity ρ of GaN and the measurement result according to the present invention, where the lateral axis represents the Hall measurement result, and the longitudinal axis represents the measurement result according to the present invention.

The sample of GaN put to use has a square shape of 15 mm×15 mm and has a thickness of 0.1 mm to 1 mm. The sample is an as-grown crystal that is not subjected to processing or polishing on the measurement surface. The result of measurement of the reflectivity and the calculated value are shown in FIG. 6. The solid line represents a measurement result, and the dotted line represents a calculated value. The measurement result and the calculated value match with each other. A high reflection is seen at equal to or more than 17 THz and equal to or less than 20 THz. Also, change in the reflectivity is confirmed at equal to or more than 21 THz and equal to or less than 23 THz. A reference frequency was selected at equal to or more than 17 THz and equal to or less than 20 THz, and a measurement frequency was selected at equal to or more than 21 THz and equal to or less than 23 THz or at a frequency less than 17 THz, whereby the mobility and the electric resistivity were calculated from the relative reflectivity obtained by the measurements. The results are shown in Table 3. Also, Table 3 shows together the mobility $\mu_{Hall}$ and the electric resistivity $\rho_{Hall}$ determined by the Hall measurement. The result of comparing the results of the terahertz measurement and the Hall measurement on the mobility is shown in FIG. 7. Also, the result of comparing the results of the terahertz measurement and the Hall measurement on the electric resistivity is shown in FIG. 8. The terahertz measurement result coincides with the Hall measurement result, and the carrier density N is shown in FIG. 5 relative to the relative reflectivity $R_{rr}$. The relationship between $R_{rr}$ and N is found out and the relationship between N and γ is clear. Therefore, by measuring the reflectivity in the two kinds of frequencies, that is, the reference frequency and the measurement frequency, the decay constant and the density of carriers can be respectively calculated, whereby the mobility and the electric resistivity can be determined.

TABLE 3

| Samples | μ (cm²V⁻¹s⁻¹) | ρ (Ω cm) | $\mu_{Hall}$ (cm²V⁻¹s⁻¹) | $\rho_{Hall}$ (Ω cm) |
|---|---|---|---|---|
| 1 | 640 | 0.290 | 654 | 0.365 |
| 2 | 508 | 0.0291 | 504 | 0.0291 |
| 3 | 432 | 0.0193 | 378 | 0.0160 |
| 4 | 302 | 0.0121 | 302 | 0.0119 |

Besides, this, regarding SiC, GaAs, GaP, GaSb, InN, InP, InAs, InSb, AlN, AlP, AlAs, AlSb, ZnS, ZnSe, ZnTe, CdS, CdSe, and CdTe also, it seems that the mobility and the electric conductivity can be calculated by radiating two terahertz waves of a reference band in which the reflectivity is constant without depending on the decay constant and the density of carriers and a measurement band in which the reflectivity changes by depending on the decay constant and the density of carriers, and comparing the reflectivities of the two optical waves.

Example 2

Figure 9:
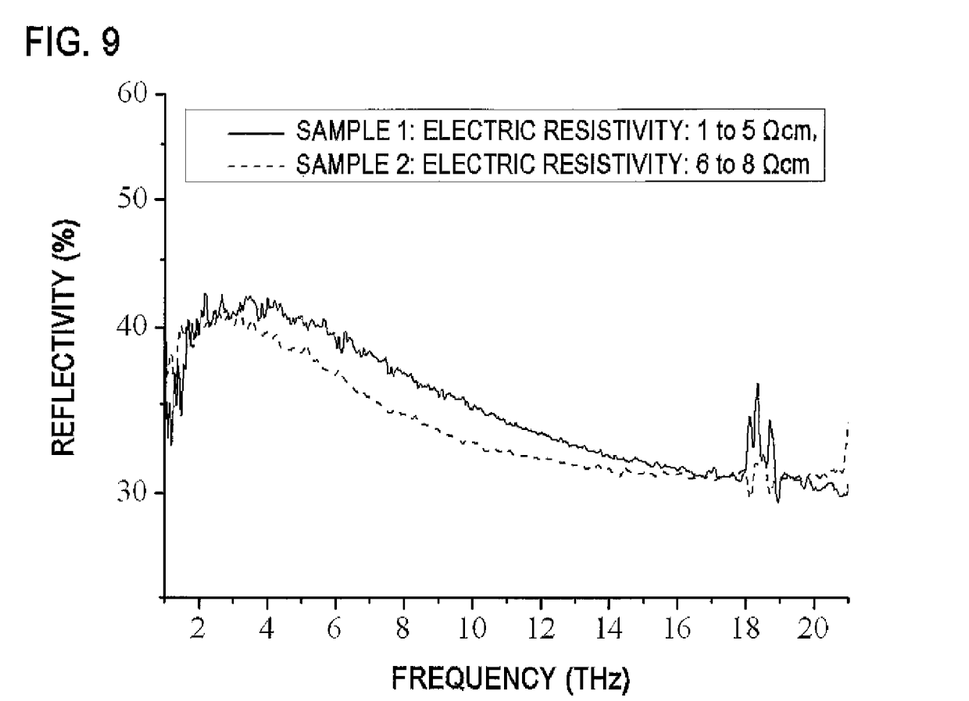
FIG. 9 is a view showing a reflectivity measurement result of silicon to terahertz waves.

The sample of silicon put to use has a circular shape with a diameter of 2 inches and has a thickness of 0.1 mm to 1 mm. Samples with a known electric resistance were used. The result of measurement of the reflectivity is shown in FIG. 9. A difference is seen in the reflection spectrum due to the difference in the electric conductivity. Therefore, by selecting a reference frequency from the frequencies of equal to or more than 3 THz and equal to or less than 4 THz having a high reflectivity and selecting a measurement frequency from the frequencies of equal to or more than 4 THz and equal to or less than 18 THz at which the reflection spectrum changes, and measuring the reflectivity in the two kinds of frequencies, that is, the reference frequency and the measurement frequency, the decay constant and the density of carriers can be respectively calculated, whereby the mobility and the electric resistivity can be determined.

Besides, this, regarding Ge also, it seem that the mobility and the electric conductivity can be calculated by radiating two terahertz waves of a reference band in which the reflectivity is constant without depending on the decay constant and the density of carriers and a measurement band in which the reflectivity changes by depending on the decay constant and the density of carriers, and comparing the reflectivities of the two optical waves.

It is apparent that the present invention is not limited to the above embodiment, and may be modified and changed without departing from the scope and spirit of the invention.

What is claimed is:

1. A mobility measuring apparatus for measuring a mobility μ of carriers in a semiconductor, comprising:
a storage unit that stores a relationship between the mobility μ and a decay constant γ of the carriers, a relationship between said decay constant γ and a carrier density N of said semiconductor and a relationship between a reflectivity R of said semiconductor to a terahertz light and said carrier density N, wherein said decay constant γ changes linearly relative to said carrier density N in said relationship between said decay constant μ and a carrier density N;
a light radiating unit that radiates a terahertz light to the semiconductor as a sample;
a detecting unit that detects a reflected light of said sample to said radiated terahertz light;
a reflectivity calculating unit that calculates a reflectivity $R_{exp}$ of said sample by determining a ratio of an intensity of said reflected light relative to an intensity of said radiated terahertz light;
an obtaining unit that obtains a carrier density $N_{exp}$ of said sample corresponding to the reflectivity $R_{exp}$ of said sample by making reference to said stored relationship between said reflectivity R and said carrier density N and obtains a decay constant $\gamma_{exp}$ of said sample corresponding to said obtained carrier density $N_{exp}$ by making reference to said stored relationship between said carrier density N and said decay constant γ, wherein said decay constant $\gamma_{exp}$ is calculated by detecting said decay constant γ that corresponds to said obtained carrier densit $N_{exp}$ in said relationship between said decay constant γ and a carrier density N, wherein said relationship between said decay constant γ and a carrier density N is obtained by fitting a plurality of plots of a relationship between said decay constant γ0 and said carrier density N; and
a mobility calculating unit that calculates said mobility $\mu_{exp}$ of said sample from said stored relationship between said mobility μ and said decay constant γ on the basis of said obtained decay constant $\gamma_{exp}$.

2. The mobility measuring apparatus according to claim 1, wherein said light radiating unit radiates a terahertz light of equal to or more than 1.5 THz and equal to or less than 40 THz.

3. The mobility measuring apparatus according to claim 1, wherein said storage unit stores said relationship between said reflectivity R and said decay constant γ by assuming that said reflectivity R to the terahertz light of a measurement band in which the reflectivity R of said semiconductor to said terahertz light changes by depending on the decay constant γ of said carriers is a measurement reflectivity $R(\omega_{out})$, assuming that said reflectivity R to the terahertz light of a reference band in which the reflectivity R of said semiconductor to said terahertz light does not change by depending on the decay constant γ of said carriers is a reference reflectivity $R(\omega_{in})$, calculating a relative reflectivity $R_{rr}$ by comparing said measurement reflectivity $R(\omega_{out})$ and said reference reflectivity $R(\omega_{in})$, and assuming said calculated relative reflectivity $R_{rr}$ to be said reflectivity R.

4. The mobility measuring apparatus according to claim 3, wherein
said light radiating unit respectively radiates the terahertz light of said measurement band and the terahertz light of said reference band to said sample, said reflectivity calculating unit calculates the relative reflectivity $R_{rrexp}$ of said sample by comparing the measurement reflectivity $R(\omega_{out})_{exp}$ calculated when the terahertz light of said measurement band is radiated and the reference reflectivity $R(\omega_{in})_{exp}$ calculated when the terahertz light of said reference band is radiated, and said obtaining unit obtains said decay constant $\gamma_{exp}$ of said sample corresponding to said calculated relative reflectivity $R_{rrexp}$ of said sample by making reference to said stored relationship between said relative reflectivity $R_{rr}$ and said decay constant $\gamma$.

5. The mobility measuring apparatus according to claim 3, wherein said reference band is a high reflection band between a TO phonon frequency and an LO phonon frequency.

6. The mobility measuring apparatus according to claim 3, wherein
said semiconductor is gallium nitride,
said measurement band is equal to or more than 21 THz and equal to or less than 23 THz, and
said reference band is equal to or more than 17 THz and equal to or less than 20 THz.

7. The mobility measuring apparatus according to claim 3, wherein
said semiconductor is silicon,
said measurement band is equal to or more than 4 THz and equal to or less than 18 THz, and
said reference band is equal to or more than 3 THz and equal to or less than 4 THz.

8. A mobility measuring method for measuring a mobility $\mu$ of carriers in a semiconductor, comprising:
obtaining a relationship between the mobility $\mu$ of the carriers and a decay constant $\gamma$ of the carriers, a relationship between said decay constant $\gamma$ and a carrier density N of said semiconductor and a relationship between a reflectivity R of said semiconductor to a terahertz light and said carrier density N, wherein said decay constant $\gamma$ changes linearly relative to said carrier density N in said relationship between said decay constant $\gamma$ and a carrier density N;
radiating a terahertz light to said semiconductor as a sample;
detecting a reflected light of said semiconductor to said radiated terahertz light;
calculating a reflectivity $R_{exp}$ of said sample by determining a ratio of an intensity of said reflected light relative to an intensity of said radiated terahertz light;
obtaining a carrier density $N_{exp}$ of said sample corresponding to the reflectivity $R_{exp}$ of said sample by making reference to said stored relationship between said reflectivity R and said carrier density N and obtaining a decay constant $\gamma_{exp}$ of said sample corresponding to said obtained carrier density $N_{exp}$ by making reference to said stored relationship between said carrier density N and said decay constant $\gamma$, wherein said decay constant $\gamma_{exp}$ is calculated b detecting said decay constant $\gamma$ that corresponds to said obtained carrier density $N_{exp}$ in said relationshi between said decay constant $\gamma$ and a carrier density $N_{exp}$, wherein said relationship between said decay constant $\gamma$ and a carrier density N is obtained by fitting a plurality of plots of a relationship between said decay constant $\gamma$ and said carrier density N; and
calculating said mobility $\mu_{exp}$ of said sample from said stored relationship between said mobility $\mu$ and said decay constant $\gamma_{exp}$ on the basis of said obtained decay constant $\gamma_{exp}$.

9. An electric resistivity measuring apparatus for measuring an electric resistivity $\rho$ of a semiconductor, comprising:

a storage unit that respectively stores a relationship between said electric resistivity $\rho$, a decay constant $\gamma$ of carriers in said semiconductor, and a carrier density N, a relationship between a reflectivity R of said semiconductor to a terahertz light and said carrier density N, and a relationship between said carrier density N and said decay constant $\gamma$, wherein said decay constant v changes linearly relative to said carrier density N in said relationship between said decay constant $\gamma$ and a carrier density N;

a light radiating unit that radiates a terahertz light to said semiconductor as a sample;

a detecting unit that detects a reflected light of said sample to said radiated terahertz light;

a reflectivity calculating unit that calculates a reflectivity $R_{exp}$ of said sample by determining a ratio of an intensity of said reflected light relative to an intensity of said radiated terahertz light;

an obtaining unit that obtains a carrier density $N_{exp}$ of said sample corresponding to the reflectivity $R_{exp}$ of said sample by making reference to said stored relationship between said reflectivity R and said carrier density N and obtains a decay constant $\gamma_{exp}$ of said sample corresponding to said obtained carrier density $N_{exp}$ by making reference to said stored relationship between said carrier density N and said decay constant $\gamma$, wherein said decay constant $\gamma_{exp}$ is calculated by detecting said decay constant $\gamma$ that corresponds to said obtained carrier density $N_{exp}$ in said relationship between said decay constant $\gamma$ and a carrier density N, wherein said relationship between said decay constant $\gamma$ and a carrier density N is obtained by fitting a plurality of plots of a relationship between said decay constant $\gamma$ and said carrier density N; and a resistivity calculating unit that calculates said electric resistivity $\rho_{exp}$ of said sample from said stored relationship between said electric resistivity $\rho$, said decay constant $\gamma$, and said carrier density N on the basis of said obtained carrier density $N_{exp}$ and said obtained decay constant $\gamma_{exp}$.

10. The resistivity measuring apparatus according to claim 9, wherein said storage unit stores said relationship between said reflectivity R and said carrier density N by assuming that said reflectivity R to the terahertz light of a measurement band in which the reflectivity R of said semiconductor to said terahertz light changes by depending on said carrier density N is a measurement reflectivity $R(\omega_{out})_{exp}$, assuming that said reflectivity R to the terahertz light of a reference band in which the reflectivity R of said semiconductor to said terahertz light does not change by depending on said carrier density N is a reference reflectivity $R(\omega_{in})_{exp}$, calculating a relative reflectivity $R_{rr}$ by comparing said measurement reflectivity R($\omega$out)exp and said reference reflectivity $R(\omega_{in})_{exp}$, and assuming said calculated relative reflectivity $R_{rr}$ to be said reflectivity R.

11. The resistivity measuring apparatus according to claim 10, wherein
said light radiating unit respectively radiates the terahertz light of said measurement band and the terahertz light of said reference band to said sample,
said reflectivity calculating unit calculates the relative reflectivity $R_{rrexp}$ of said sample by comparing the measurement reflectivity $R(\omega_{out})_{exp}$ calculated when the terahertz light of said measurement band is radiated and the reference reflectivity $R(\omega_{in})_{exp}$ calculated when the terahertz light of said reference band is radiated, and said obtaining unit obtains said carrier density $N_{exp}$ of said sample corresponding to said calculated relative reflectivity $R_{rrexp}$ of said sample by making reference to said stored relationship between said relative reflectivity $R_{rr}$ and said carrier density N.

12. The resistivity measuring apparatus according to claim 10, wherein said reference band is a high reflection band between a TO phonon frequency and an LO phonon frequency.

13. The resistivity measuring apparatus according to claim 10, wherein
said semiconductor is gallium nitride,
said measurement band is equal to or more than 21 THz and equal to or less than 23 THz, and
said reference band is equal to or more than 17 THz and equal to or less than 20 THz.

14. The resistivity measuring apparatus according to claim 10, wherein
said semiconductor is silicon,
said measurement band is equal to or more than 4 THz and equal to or less than 18 THz, and
said reference band is equal to or more than 3 THz and equal to or less than 4 THz.

15. An electric resistivity measuring method for measuring an electric resistivity ρ of a semiconductor, comprising:
respectively obtaining a relationship between said electric resistivity ρ, a decay constant γ of carriers in said semiconductor, and a carrier density N, a relationship between a reflectivity R of said semiconductor to a terahertz light and said carrier density N, and a relationship between said carrier density N and said decay constant γ, wherein said decay constant v changes linearly relative to said carrier density N in said relationship between said decay constant v and a carrier density N;
radiating a terahertz light to said semiconductor constituting a sample;
detecting a reflected light of said sample to said radiated terahertz light;
calculating a reflectivity $R_{exp}$ of said sample by determining a ratio of an intensity of said reflected light relative to an intensity of said radiated terahertz light;
obtaining a carrier density $N_{exp}$ of said sample corresponding to the reflectivity $R_{exp}$ of said sample by making reference to said stored relationship between said reflectivity R and said carrier density N and obtaining a decay constant $\gamma_{exp}$ of said sample corresponding to said obtained carrier density $N_{exp}$ by making reference to said stored relationship between said carrier density N and said decay constant γ, wherein said decay constant $\gamma_{exp}$ is calculated b detecting said decay constant γ that corresponds to said obtained carrier density $N_{exp}$, in said relationship between said decay constant γ and a carrier density N, wherein said relationship between said decay constant γ and a carrier density N is obtained by fitting a plurality of plots of a relationship between said decay constant γ and said carrier density N; and
calculating said electric resistivity $\rho_{exp}$ of said sample from said stored relationship between said electric resistivity ρ, said decay constant γ, and said carrier density N on the basis of said obtained carrier density $N_{exp}$ and said obtained decay constant $\gamma_{exp}$.

\* \* \* \* \*